(12) United States Patent
Magnuson

(10) Patent No.: US 8,011,079 B2
(45) Date of Patent: *Sep. 6, 2011

(54) METHOD OF INCORPORATING A TIP INTO AN ENDOVASCULAR DEVICE

(75) Inventor: Mark A. Magnuson, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/537,127

(22) Filed: Aug. 6, 2009

(65) Prior Publication Data
US 2010/0031491 A1 Feb. 11, 2010

Related U.S. Application Data

(63) Continuation of application No. 11/842,514, filed on Aug. 21, 2007, now Pat. No. 7,578,042.

(51) Int. Cl.
*A61M 25/16* (2006.01)
*B21D 39/00* (2006.01)

(52) U.S. Cl. .............................. 29/521; 29/557; 604/533
(58) Field of Classification Search .................. 29/428, 29/516, 520, 521, 525, 557; 604/533
See application file for complete search history.

(56) References Cited

U.S. PATENT DOCUMENTS

| 5,263,945 | A | 11/1993 | Byrnes et al. |
| 5,879,499 | A | 3/1999 | Corvi |
| 6,332,877 | B1 | 12/2001 | Michels |
| 7,578,042 | B2 * | 8/2009 | Magnuson ...................... 29/521 |
| 2007/0287957 | A1 | 12/2007 | Magnuson et al. |

* cited by examiner

*Primary Examiner* — Jermie E Cozart
(74) *Attorney, Agent, or Firm* — Brinks Hofer Gilson & Lione

(57) ABSTRACT

An endovascular device tip assembly and method of making the same, incorporating a tip device with a first and second flange, usable with catheters and other suitable endovascular devices is provided. The tip assembly incorporates a tip device by providing a counterbore within a primary bore of a tubular end portion of an endovascular device. The tip device is fitted securely within the counterbore by placing the first flange within the counterbore and the second flange on the outside of the end portion.

13 Claims, 3 Drawing Sheets

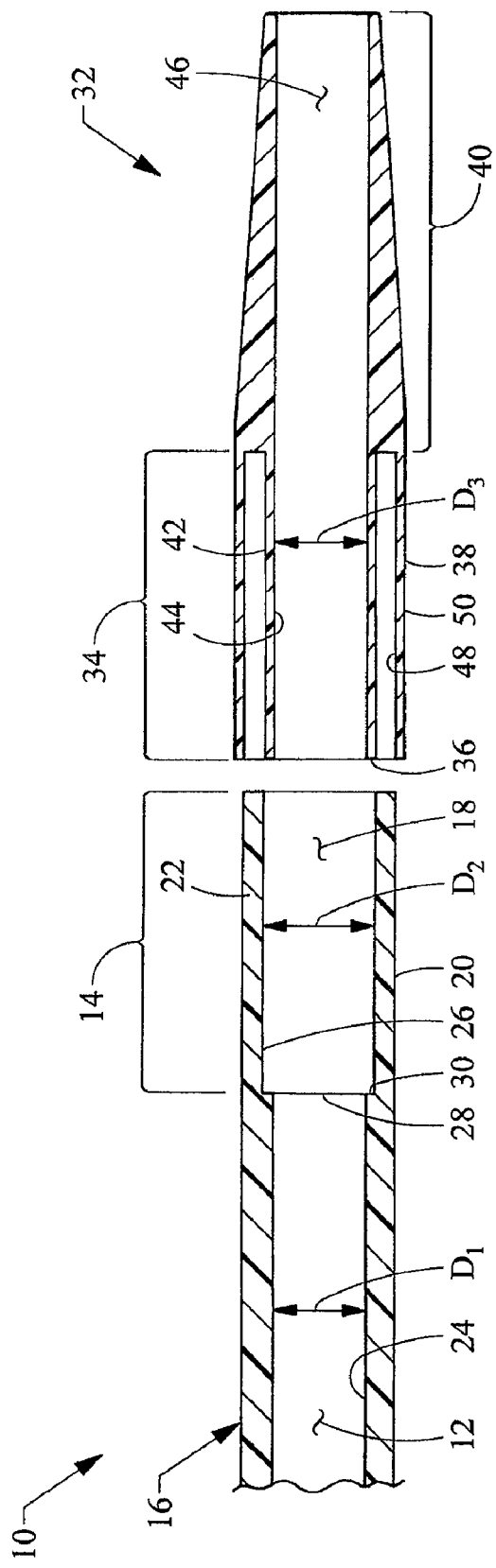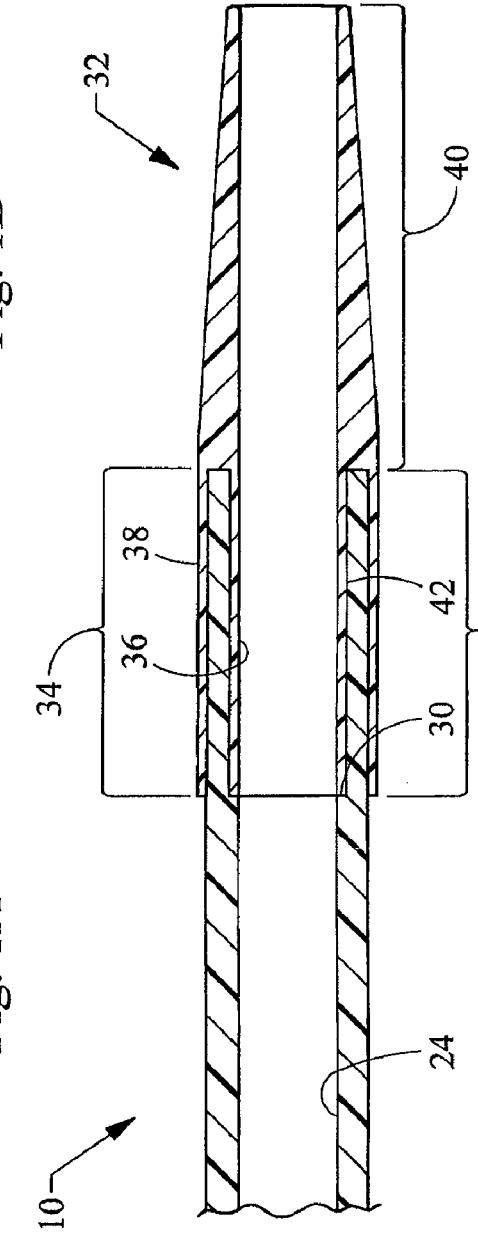

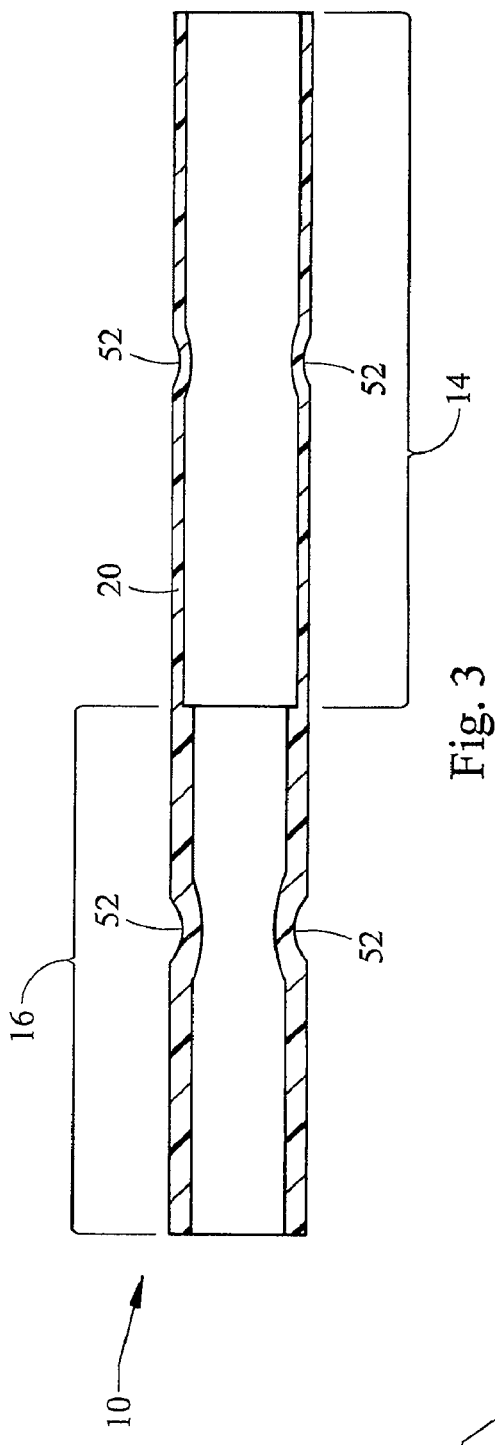
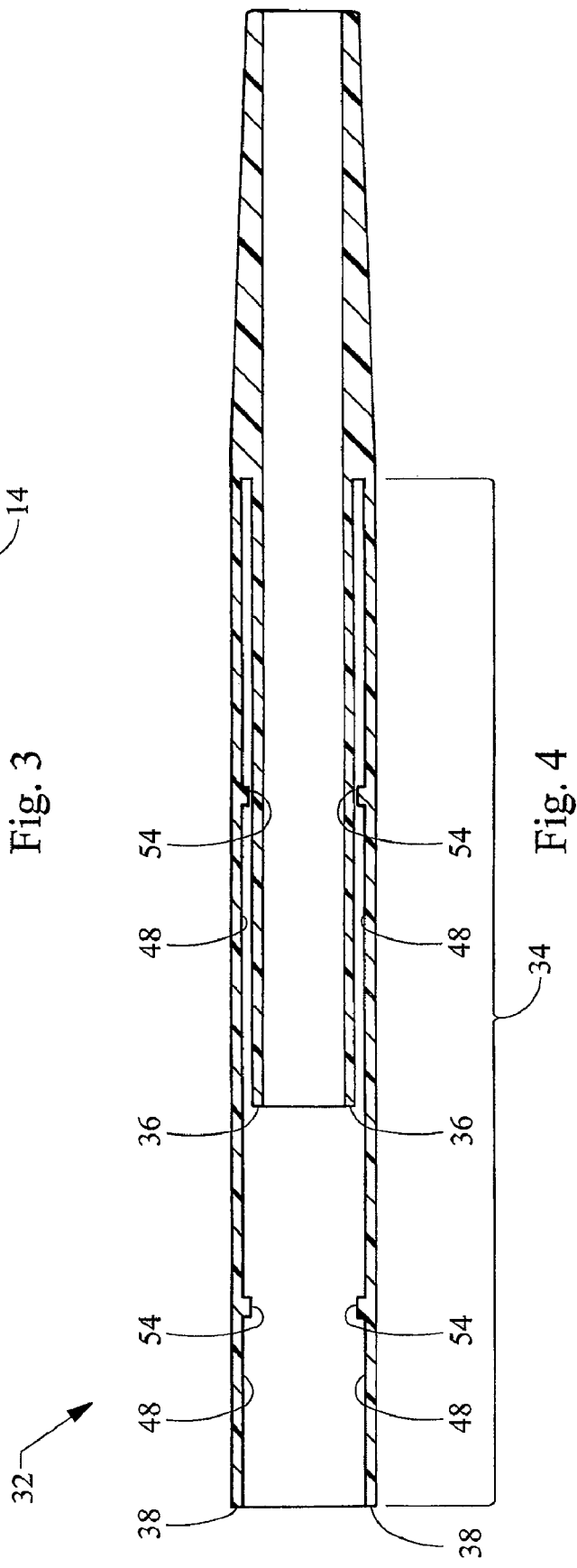
Fig. 3
Fig. 4

METHOD OF INCORPORATING A TIP INTO AN ENDOVASCULAR DEVICE

CROSS-REFERENCE TO RELATED APPLICATIONS

This application is a continuation of U.S. application Ser. No. 11/842,514, filed Aug. 21, 2007, now U.S. Pat. No. 7,578,042 B2 the entire contents of which are hereby incorporated by reference.

BACKGROUND

The present application relates to an endovascular device tip assembly. Moreover, this application relates to the use of a low profile tip which is disposed at the end of a medical device, such as a catheter, by counterboring the distal end of a tubular device and placing the tip within.

Endovascular devices have long been known which can be surgically inserted into a body lumen, such as an artery, to reinforce, support, repair, or otherwise enhance the performance of the lumen. For example, catheters generally include a hollow tubular portion, usually formed of resilient plastic, for insertion through the skin of a patient into a cavity, duct or vessel to permit injection or withdrawal of fluids, or to deliver medications to patients for therapeutic reasons.

Typically, the distal tip of an endovascular device consists of a hollow metal or polymer cylinder which is tapered along the outer surface. The inside diameter of the tip is typically sized to allow the smooth passage of a guidewire of a given diameter. Preferably, the inside diameter remains constant. Therefore, it is desirable to develop a method of incorporating the tip of an endovascular device without changing the inner diameter of the tip, which would make it more difficult to pass a guidewire therethrough. This invention addresses such a method for incorporating a tip of an endovascular device.

BRIEF SUMMARY

The endovascular tip device described below may overcome the aforementioned problems and relates to a medical device, and more particularly, to an endovascular tip device assembly and method of making the same that is designed to yield a smooth inner surface of a medical device.

A method of incorporating an endovascular device tip is disclosed. This method comprises incorporating a tip into an endovascular device comprising by providing a tubular end portion of an endovascular device comprising a distal end portion and at least one longitudinal bore extending therethrough. The distal end portion comprising at least one outlet opening and at least one longitudinal bore having an internal diameter. The method further includes creating a counterbore through the distal end of the tubular end portion, thereby increasing the internal diameter of at least one longitudinal bore, providing a tip having at least a first and second flange, and positioning the first flange within the counterbore and the second flange adjacent an outer surface of the tubular end portion, the tip having a first end and a second end.

The method described above, wherein the internal diameter of at least one longitudinal bore is approximately equal to an internal diameter of the tip.

The method described above, wherein the internal diameter of the counterbore is approximately from about 0.001 inches to about 0.125 inches larger than the internal diameter of at least one longitudinal bore.

The method described above, wherein the internal diameter of the counterbore is approximately 0.004 inches larger than the internal diameter of at least one longitudinal bore.

The method described above, wherein at least one longitudinal bore is further defined by an outer radial surface and an inner radial surface; and wherein the counterbore is further defined by a first end and a second end defining a ledge between the inner radial surface of at least one longitudinal bore and an inner surface of the counterbore; and wherein the first end of the tip is adjacent the ledge.

The method described above, wherein the first flange is disposed within the inner surface of the counterbore and the second flange is disposed adjacent the outer radial surface of at least one longitudinal bore.

The method as described above, wherein the ledge is approximately 0.0005 to about 0.0625 inches thick and the first flange of the tip has a thickness approximately equal to said ledge.

The method as described above, wherein the ledge is approximately 0.002 inches thick and the first flange of the tip has a thickness approximately equal to the ledge.

An endovascular tip device manufactured according to the method as described above.

The method described above, wherein the tubular end portion has at least a first pair of openings in the distal end portion and at least a second pair of openings in the proximal end portion; and the tip has at least a first pair of locking members protruding from an interior surface of a proximal end portion of the second flange and at least a second pair of locking members protruding from the interior surface of the second flange, wherein the second pair of locking members is disposed distally of the first pair of the locking members, along the interior surface of the second flange.

An endovascular device is disclosed comprising a tubular end portion of the endovascular device having a distal end portion and a proximal end portion, the distal end portion having an internal diameter larger than an internal diameter of the proximal end portion. The endovascular device further includes the tubular end portion, which is by an annular wall, the annular wall having at least one opening in the distal end portion and at least one opening in the proximal end portion and a tip device having a first end disposed within the distal end portion of the tubular end portion and having a first flange and a second flange. The second flange has at least one locking member protruding inwardly from an interior surface of the second flange, which mates with at least one opening in the distal end portion of the tubular end portion.

The endovascular device as described above, wherein the tubular end portion has at least a first pair of openings in the distal end portion and at least a second pair of openings in the proximal end portion, and the tip device having at least a first pair of locking members protruding from the interior surface of the proximal portion of the second flange and at least a second pair of locking members protruding from the interior surface of the second flange, wherein the second pair of locking members are disposed distally of the first pair of locking members, along the interior surface of the second flange.

The endovascular device as described above, wherein the first pair of locking members mate with the first pair of openings and the second pair of locking members mate with the second pair of openings to secure the tip device to the tubular end portion.

The endovascular device as described above, wherein the tubular end portion and the tip device are formed of different materials.

BRIEF DESCRIPTION OF THE DRAWINGS

FIG. 1A is cross-sectional view of an endovascular device prior to incorporation of a tip;

FIG. 1B is a cross-sectional view of an endovascular tip prior to incorporation with the endovascular device;

FIG. 2 is a cross-sectional view of an embodiment of an endovascular device and tip;

FIG. 3 is cross-sectional view of an endovascular device prior to incorporation of a tip;

FIG. 4 is a cross-sectional view of an endovascular tip prior to incorporation with the endovascular device.

DETAILED DESCRIPTION

Figure 5:
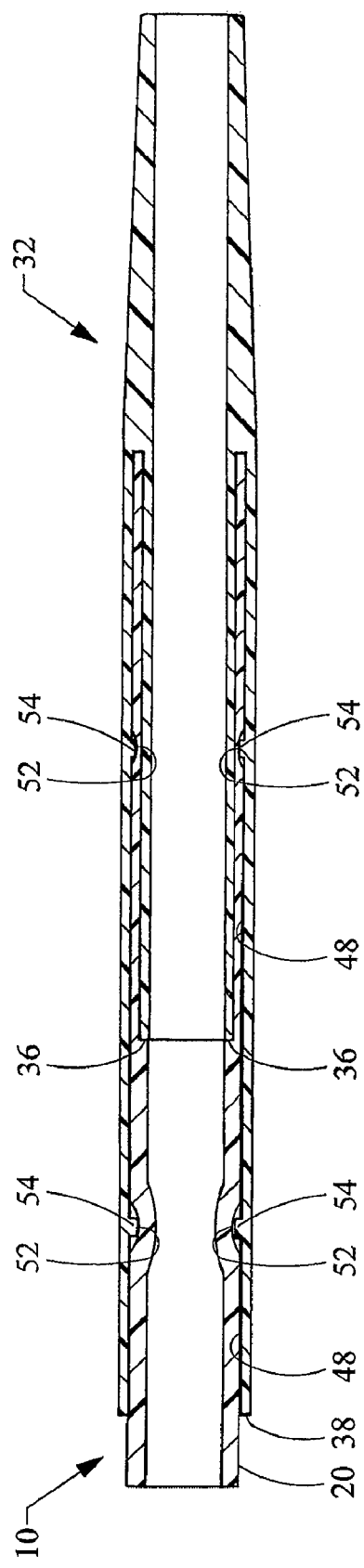
FIG. 5 is a cross-sectional view of an embodiment of an endovascular device and tip.

An exemplary embodiment of the present invention may be described in use with any endovascular device, but for the purposes of this application, will be referred to as a catheter. To be clear, the tip assembly will be described in accordance with the following method, but other methods are contemplated by the invention.

Referring now to FIGS. 1A and 1B, a method for incorporating a tip of an endovascular device into, for example a catheter, includes providing a tubular end portion 10 of any desired length having a primary bore 12 for directing fluids or mechanical devices, such as stents, to and from the body of the patient. The tubular end portion 10 may be integral with the catheter body of a single lumen catheter system, such as a balloon catheter. On catheter based systems that include multiple lumens, the distal end portion may be integral with the innermost lumen. Alternatively, the tubular end portion 10 may be glued or heat molded to the outermost catheter body. This technique may result in a larger overall profile of the distal end of the catheter-based system.

As shown in FIG. 1A, the tubular end portion 10 of a catheter body includes a distal end portion 14 and a proximal end portion 16. The distal end portion 14 may define an outlet opening 18 of the primary bore 12. The tubular end portion 10 also may include an annular side wall 20 having an outer radial surface 22 and an inner radial surface 24 further defining the bore 12 of the end portion 10. The tubular end portion 10 of the catheter body may be formed of any appropriate material which may be inserted into the human body, but is preferably formed of a flexible material such as nickel-titanium alloys, polyethylene, nylon, PVC, polyurethane or silicone. The tubular end portion 10 may also include various support structures, such as woven or helical reinforcements. The reinforcements may be in the form of wires or bands.

The inner radial surface 24 of the side wall 20 may include a first inner diameter D1. The first inner diameter D1 may generally be between about 0.010 inches to about 0.25 inches, and may desirably be about 0.017 inches in diameter. Generally, the side wall 20 of the catheter body may be about 0.004 inches thick, measured from the outer radial surface 22 to the inner radial surface 24 of the bore 12. Alternatively, the side wall 20 may range from about 0.001 to about 0.125 inches thick.

Referring again to FIG. 1A, the method further includes forming a counterbore 26 within the end portion 10. The counterbore 26 is generally created within the distal end portion 14. The counterbore 26 may be created in an unmodified tube in a variety of ways. Preferably, but not limited to, the inner radial surface 24 of the bore 12 may be prepared by drilling or grinding the counterbore 26 into the distal end portion 14. The counterbore 26 may also be formed during the molding process of the catheter body or may be cut or reformed into the tubular end portion 10 after the catheter is formed.

Starting at or about the outlet opening 18 of the end portion 10, the counterbore 26 may be formed within the annular side wall 20 of the catheter body, lengthwise, toward the proximal end portion 16. The counterbore 26 provides an enlarged inner diameter, or a secondary inner diameter D2, within a portion of the bore 12. The counterbore 26 may decrease the thickness of the side wall 20 by approximately half of the original wall thickness. One embodiment of the present invention includes a wall thickness of about 0.004 inches. The resulting secondary inner diameter D2 may be about 0.014 to about 0.254 inches, depending on the original thickness of the initial inner diameter of the end portion 10. For example, if D1 is originally 0.017 inches, the resulting inner diameter of the bore D2 may be approximately 0.021 inches where the wall thickness is approximately 0.004 inches.

The proximal end 28 of the counterbore 26 generally forms a ledge 30 within the tubular end portion 10 of the catheter body. This ledge 30 is generally the same thickness of a first flange 36 of a tip 32, described below, that is to be incorporated into the end portion 10. Such a first flange 36 may generally be about 0.002 inches thick. The thickness of the first flange 36 and the ledge 30 generally correspond to the size of the counterbore 26. Preferably, the flange 36 is annular in shape and forms a full cylinder around the inner surface of the tip 32.

Referring now to FIG. 1B, the method further includes providing a tip 32, formed of a suitable material. The tip 32 may be formed of plastic or polymer based material. The inside diameter D3 of the tip 32 is typically sized to allow the consistent passage of a guide wire of a given diameter. As shown in FIG. 1B, the tip 32 includes a proximal end portion 34 with a first flange 36 and a second flange 38. The space between the flanges, 36, 38, respectively, may be sized to receive the distal end portion 14 of the annular wall 20 of the tubular end portion 10. As shown in FIG. 2, positioning the distal end 14 of the tubular end portion 10 between the first flange 36 and second flange 38 of the tip 32 may create a friction-type fitting between the end portion 10 and the tip 32.

The first flange 36 and second flange 38 may extend approximately half the length of the tip 32. The first and second flanges 36, 38 are generally disposed at the proximal end 34 of the tip 32. The flanges 36, 38 may form concentric circles with approximately 0.004 inches between them. The resulting space between the flanges 36, 38 creates a cavity to receive the distal end 14 of the tubular end portion 10. The distal end 40 of the tip 32 may generally be solid and tapered to easily move through the intended vessel.

Referring again to FIG. 1B, the first flange 36, as described above, is generally circular, having an outer radial surface 42 and an inner radial surface 44. The inner radial surface 42 of the first flange 36 defines a second longitudinal bore 46 which terminates at the proximal end 34 of the tip 32 and at a second, distal end 40. The proximal end 34 of the tip 32 may be manually positioned adjacent the ledge 30 of the counterbore 26 so that the inner radial surface 42 of the first flange 36 extends no further radially inward than the inner radial surface 24 of the bore 12 of the tubular end portion 10 of the catheter body. (See FIG. 2) As a result, the inner radial surface 24 of the bore 12 is substantially constant without interruptions or inwardly extending ridges formed by the proximal 34 and distal ends 40 of the tip 32. The tip 32 may also be placed within the counterbore 26 by use of an automated machine or method, such as insert molding.

Because the inner radial surface 24 of the tubular end portion 10 remains substantially constant, it prevents the formation of internal restrictions in the primary bore 12 thereby maintaining a constant inner diameter D1 and D3.

Referring to FIG. 1B, the outer flange 38 may also have an inner 48 and an outer 50 radial surface. The inner surface 48 of the outer flange 38 may be fitted against the outer surface 22 of the distal end 14 of the tubular end portion 10.

Moreover, the tip 32 may be tapered at the distal end 40. One way to taper the tip 32 is by heating and/or applying pressure to the distal end portion 40. The tip 32 may be reformed to a desired diameter, generally accommodating the diameter of the wire guide to be used with the device. The tip 32 may generally be preformed and tapered before insertion within the catheter body. The tip 32 may also be insert molded onto the catheter body 10.

When dissimilar plastic materials are used for the tip 32 and the tubular end portion 10, a mechanical lock may be incorporated into the device. As shown in FIG. 3, mechanical locks may be incorporated into the device by providing a series of holes 52 along the annular wall 20 of the tubular end portion 10. The holes 52 may be approximately 0.020 inches in diameter, with at least one set of holes 52 that may be formed in the distal 14, counter bored portion, of the tubular end portion 10 and at least one set of holes 52 that may be formed in the proximal 16, un-bored portion, of the tubular end portion 10.

As shown in FIGS. 4 and 5, after the tip is pressed onto the distal end of the catheter, the holes 52 are filled by mating corresponding locking members 54 on the inner radial surface 48 of the second flange 38 to lock the tip in place. The second flange 38 may extend beyond the inner flange 36 to provide extra locking members 54 on the tip 32. In this embodiment, the inner radial surface 48 of the second flange 38 may include one set of locking members 54 on the proximal end 34 (FIG. 4) which may mate with the holes 52 provided in the proximal end 16 (FIG. 3), or the un-bored portion, of the tubular end portion 10. Similarly, the second flange 38 may include a second set of locking members 54 distal of the first set, but positioned to mate with the holes in the annular wall 20 of the distal 14 (FIG. 3), counter-bored portion, of the tubular end portion 10.

Referring now to FIG. 5, the proximal end 34 of the tip 32 is inserted into, and flush with, the ledge 30 of the counterbore 26 in the tubular end portion 10, as described above, with the second flange 38 extending past the counterbore 26. The tip 32 and the end portion 10 are then effectively mechanically locked together. Additional locking mechanisms may be used in addition to the mechanical mechanisms described above, such as heat bonding or gluing.

In use, the tubular end portion 10 of the endovascular device is inserted into a patient's body to perform one or more of a variety of functions including the delivery and withdrawal of fluids and mechanical devices such as stents. As is apparent, the present invention may be used to incorporate tips 32 formed of various suitable materials into many different types of endovascular devices including delivery catheters, angioplasty balloons and other endoscopic instrumentation.

It is therefore intended that the foregoing detailed description be regarded as illustrative rather than limiting, and that it be understood that it is the following claims, including all equivalents, that are intended to define the spirit and scope of this invention.

The invention claimed is:

1. A method of incorporating a tip into an endovascular device comprising:
    providing an endovascular device having a tubular end portion, the tubular end portion comprising a proximal portion and a distal end portion, an outlet opening formed in the distal end portion, a longitudinal bore extending through the distal end portion and in communication with the outlet opening, a counterbore formed in the distal end portion and having an increased internal diameter relative to an internal diameter of the proximal portion, and a first engagement member formed in the distal end portion;
    providing a hollow tubular tip comprising a proximal end portion having first and second annular flanges, the first flange being disposed within and spaced apart from the second flange, and a second engagement member formed in one of the first and second flanges;
    positioning the first flange within the counterbore and positioning the second flange over an outer radial surface of the distal end portion of the tubular end portion; and
    securing the tip onto the tubular end portion by mating the first engagement member with the second receiving member.

2. The method of claim 1, wherein the second engagement member comprises a outwardly projecting locking member.

3. The method of claim 1, wherein the first engagement member comprises an opening.

4. The method of claim 1, wherein the tubular end portion comprises a pair of second engagement members disposed in an outer surface of the distal end portion and the tip comprises a pair of first engagement members disposed on an inner surface of the second flange.

5. The method of claim 1, wherein the tubular end portion comprises a pair of second engagement members disposed in an inner surface of the distal end portion and the tip comprises a pair of first engagement members disposed on an outer surface of the first flange.

6. The method of claim 1, wherein the tubular portion further comprises a third engagement member formed in the proximal portion, and the tip further comprises a fourth engagement member formed in one of the first and second flanges, and wherein securing the tip onto the tubular end portion further comprises mating the third engagement member with the fourth engagement member.

7. The method of claim 1, wherein the counterbore is formed by one of drilling, cutting, or grinding.

8. The method of claim 1, wherein the counterbore is formed by molding the tubular end portion.

9. The method of claim 1, wherein the internal diameter of the proximal portion of the tubular member is approximately equal to an internal diameter of the first flange of the tip.

10. The method of claim 1, wherein the first flange comprises a radial thickness that is approximately equal to a radial height of a ledge formed at a proximal end of the counterbore, and the method further comprises positioning a proximal end of the tip flush against the ledge so as to form a constant internal diameter of the endovascular device.

11. The method of claim 1, wherein the first flange comprises a first longitudinal length, and wherein the second flange comprises a second longitudinal length that is greater than the first longitudinal length.

12. The method of claim 1, wherein the first flange comprises a first longitudinal length, and wherein the second flange comprises a second longitudinal length that is substantially equal to the first longitudinal length.

13. A method of incorporating a tip into an endovascular device comprising:
- providing an endovascular device having a tubular end portion, the tubular end portion comprising a proximal portion and a distal end portion, an outlet opening formed in the distal end portion, and a longitudinal bore extending through the distal end portion and in communication with the outlet opening;
- providing a hollow tubular tip comprising a proximal end portion having first and second annular flanges, the first flange being disposed within and spaced apart from the second flange;
- forming a counterbore in the distal end portion, the counterbore having an increased internal diameter relative to an internal diameter of the proximal portion;
- forming a first locking mechanism in the distal end portion of the tubular end portion;
- forming a second locking mechanism in the the proximal end portion of the tip;
- positioning the first flange within the counterbore and positioning the second flange over an outer radial surface of the distal end portion of the tubular end portion; and
- securing the tip onto the tubular end portion by mating the first locking mechanism with the second locking mechanism.

* * * * *

UNITED STATES PATENT AND TRADEMARK OFFICE
CERTIFICATE OF CORRECTION

| | | |
|---|---|---|
| PATENT NO. | : 8,011,079 B2 | Page 1 of 1 |
| APPLICATION NO. | : 12/537127 | |
| DATED | : September 6, 2011 | |
| INVENTOR(S) | : Mark A. Magnuson | |

It is certified that error appears in the above-identified patent and that said Letters Patent is hereby corrected as shown below:

In the Claims

In column 8, claim 13, line 3, after "locking mechanism in" replace "the the proximal" with --the proximal--.

Signed and Sealed this
Eighth Day of November, 2011

David J. Kappos
*Director of the United States Patent and Trademark Office*